United States Patent [19]

Takaya et al.

[11] Patent Number: 4,727,073
[45] Date of Patent: Feb. 23, 1988

[54] PYRIMIDINE DERIVATIVES AND COMPOSITION OF THE SAME

[75] Inventors: Takao Takaya, Kawanishi; Hisashi Takasugi, Osaka; Atsushi Kuno, Mino; Yoshie Sugiyama, Takarazuka, all of Japan

[73] Assignee: Fujisawa Pharmaceutical Co., Ltd., Osaka, Japan

[21] Appl. No.: 779,043

[22] Filed: Sep. 23, 1985

[30] Foreign Application Priority Data

Oct. 1, 1984 [GB] United Kingdom ............... 8424711
Apr. 15, 1985 [GB] United Kingdom ............... 8509623

[51] Int. Cl.⁴ .................. A61K 31/505; C07D 403/04
[52] U.S. Cl. .................... 514/252; 514/211;
514/222; 514/265; 540/485; 544/58.4;
544/58.6; 544/60; 544/122; 544/295; 544/242;
544/335
[58] Field of Search ............... 544/295, 335, 122, 60,
544/58.4, 58.6, 242; 540/485; 514/211, 222,
252, 269

[56] References Cited

U.S. PATENT DOCUMENTS 3,944,581 3/1976 Schwan .............................. 544/335
4,382,140 5/1983 Schwan .............................. 544/242

FOREIGN PATENT DOCUMENTS 0103796 3/1984 European Pat. Off.
0162208 11/1985 European Pat. Off. ............ 544/335

OTHER PUBLICATIONS

J. Heterocyclic Chem., 18, 183(1981); E. J. Breaux et al., An Improved General Synthesis of 4-Aryl-5-pyrimidinecarboxylates, Jan. 1981.
Arch. Pharm. (Weinheim) 314, 938–949, (1981); Klaus Görlitzer et al., 2,4-Diaryl-6-methyl-1,2,3,4-tetrahydropyrimidin-5-carbonsäureester.
Arch. Pharm. (Weinheim) 312, 591–597, (1979); Fritz Eiden et al., Über die Reaktion von 2,6-Dimethyl-4-pyron-3,5-dicarbonsäureethylester mit Aminen.

Primary Examiner—Glennon H. Hollrah
Assistant Examiner—James H. Turnipseed
Attorney, Agent, or Firm—Oblon, Fisher, Spivak, McClelland & Maier

[57] ABSTRACT

The invention relates to new pyrimidine derivatives, useful in the treatment of cerebrovascular disease, of the formula:

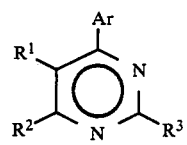

wherein Ar, $R^1$, $R^2$ and $R^3$ are defined in the specification.

11 Claims, No Drawings

PYRIMIDINE DERIVATIVES AND COMPOSITION OF THE SAME

This invention relates to new pyrimidine derivatives. More particularly, this invention relates to pyrimidine derivatives and their pharmaceutically acceptable salts which are useful in the treatment of cerebrovascular diseases, to processes for preparation thereof and to compositions containing the same.

The pyrimidine derivatives of this invention are represented by the following general formula (I):

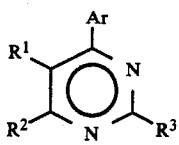

wherein

Ar is aryl group substituted with 1 to 3 substituent(s) selected from the group consisting of nitro, halo(lower)alkyl, lower alkoxy and a group of the formula:

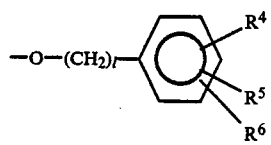

(in which l, $R^4$, $R^5$ and $R^6$ are each as defined in the below);

$R^1$ is esterified carboxy group, lower alkanoyl group, hydroxy(lower)alkyl group or a group selected from the following formulas:

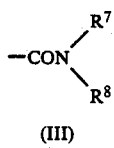 and 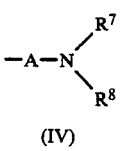

(III) (IV)

(in which $R^7$, $R^8$, and A are each as defined in the below);

$R^2$ is hydrogen, lower alkyl group or a group of the formula:

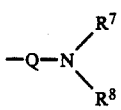

(in which Q, $R^7$ and $R^8$ are each as defined in the below);

$R^3$ is lower alkyl group or aryl group;
l is an integer of 0, 1 to 6;
$R^4$, $R^5$ and $R^6$ are each hydrogen or halogen;
$R^7$ and $R^8$ are each hydrogen, optionally substituted N-containing heterocyclic group or lower alkyl group optionally substituted with 1 to 3 substituent(s) selected from the group consisting of mono- or di-(lower)alkylamino and optionally substituted N-containing heterocyclic groups; or $R^7$ and $R^8$ are taken together to form an optionally substituted N-containing heterocyclic group with the adjacent nitrogen atom;

A and Q are each straight or branched lower alkylene group which may be substituted with a lower alkylidene;

provided that $R^1$ is a group of the formula:

(in which $R^7$, $R^8$ and A are each as defined above) when $R^2$ is hydrogen or lower alkyl group; and their pharmaceutically acceptable salts.

Particulars of the various definitions mentioned in this specification and preferred examples thereof are explained in the following.

The term "lower" used in this specification is intended to mean a group having 1 to 6 carbon atoms, unless otherwise provided.

Suitable "aryl" may include phenyl, naphthyl, diphenylyl and the like.

Suitable "halogen" may include bromo, fluoro, chloro and iodo.

Suitable "lower alkyl" may include straight or branched one such as methyl, ethyl, propyl, isopropyl, butyl, t-butyl, pentyl, hexyl and the like.

Suitable "halo(lower)alkyl" may include chloromethyl, trifluoromethyl, bromoethyl, 1-bromoethyl, dichloroethyl, iodopropyl, trichloro-t-butyl, fluoropentyl, chlorohexyl and the like.

Suitable "lower alkoxy" may include straight or branched one such as methoxy, ethoxy, propoxy, isopropoxy, butoxy, t-butoxy, pentyloxy, hexyloxy and the like.

Preferable examples of a group of the formula:

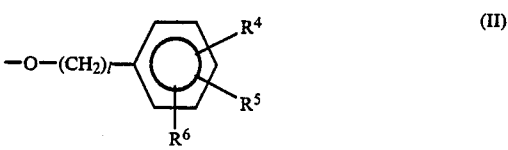

may include phenoxy, phenyl(lower)alkoxy (e.g. benzyloxy, phenethyloxy, etc.), halophenyl(lower)alkoxy (e.g., chlorobenzyloxy, dichlorophenethyloxy, fluorophenylbutoxy, bromophenylhexyloxy, etc.), and the like.

Suitable ester moiety in the "esterified carboxy" may include lower alkyl ester (e.g. methyl ester, ethyl ester, propyl ester, isopropyl ester, butyl ester, t-butyl ester, pentyl ester, hexyl ester, etc.), mono(di or tri)halo(lower)alkyl ester (e.g. iodoethyl ester, dichloroethyl ester, trichloroethyl ester, trifluoromethyl ester, etc.), hydroxy(lower)alkyl ester (e.g. hydroxymethyl ester, hydroxyethyl ester, hydroxypropyl ester, hydroxybutyl ester, etc.), ar(lower)alkyl ester (e.g. benzyl ester, 4-nitrobenzyl ester, trityl ester, etc.), and the like.

Suitable "lower alkanoyl" may include straight or branched one such as formyl, acetyl, propionyl, butyryl, valeryl, pivaloyl and the like.

Suitable "hydroxy(lower)alkyl" may include hydroxymethyl, 1-hydroxyethyl, 2-hydroxyethyl, 1-hydroxypropyl, 3-hydroxypropyl, 2-hydroxybutyl, 4- hydroxybutyl, 5-hydroxypentyl, 6-hydroxyhexyl and the like.

Suitable "N-containing heterocyclic group" may include unsaturated 5- or 6-membered heteromonocyclic group containing 1 or 2 nitrogen atom(s), for example, pyrrolyl, imidazolyl, imidazolinyl, pyrazolyl, pyridyl, pyrimidinyl, 1,2,3,6-tetrahydropyridyl, etc.; saturated 5- or 6-membered heteromonocyclic group containing 1 or 2 nitrogen atom(s) and/or 1 or 2 oxygen atom(s), for example, pyrrolidinyl, imidazolidinyl, piperidyl, piperazinyl, morpholinyl, etc.; saturated 5- or 6-membered heteromonocyclic group containing 1 or 2 nitrogen atom(s) and 1 or 2 sulfur atom(s), for example, thiazolidinyl, thiomorpholinyl, etc., and the like. Said "N-containing heterocyclic group" may have 1 to 3 substituents such as lower alkyl as exemplified above.

Preferable examples of "substituted N-containing heterocyclic group" may include lower alkylpyrrolidinyl (e.g., 1-ethylpyrrolidinyl, 2-methylpyrrolidinyl, 3-isopropylpyrrolidinyl, 1-t-butylpyrrolidinyl, 1-hexylpyrrolidinyl, etc.), lower alkylimidazolidinyl (e.g., 3-methylimidazolidinyl etc.), lower alkylpiperidyl (e.g., 1-methylpiperidyl, 1-ethylpiperidyl, 2-t-butylpiperidyl, 3-hexylpiperidyl, etc.), lower alkylpiperazinyl (e.g., 1-methylpiperazinyl, 2-ethylpiperazinyl, 3-isopropylpiperazinyl, 1-hexylpiperazinyl, etc.), lower alkylpyridyl (e.g., 1-methylpyridyl, 2-ethylpyridyl, 3-t-butylpyridyl, 1-hexylpyridyl, etc.) and the like.

Suitable "mono- or di-(lower)alkylamino" may include methylamino, ethylamino, isopropylamino, hexylamino, dimethylamino, diethylamino, dipropylamino, methylethylamino and the like.

Preferable examples of the substituted lower alkyl group for $R^7$ and $R^8$ may include mono- or di-(lower)alkylamino(lower)alkyl (e.g., methylaminomethyl, dimethylaminoethyl, diethylaminoethyl, dipropylaminoethyl, dimethylaminopropyl, diethylaminopropyl, dimethylaminobutyl, dimethylaminohexyl, etc.), morpholinyl(lower)alkyl (e.g., morpholinylmethyl, morpholinoethyl, morpholinylethyl, morpholinylpropyl, morpholinylbutyl, etc.), piperazinyl(lower)alkyl wherein piperazinyl is optionally substituted with lower alkyl (e.g. piperazinylmethyl, piperazinylethyl, piperazinylpropyl, methylpiperazinylethyl, ethylpiperazinylethyl, isopropylpiperazinylhexyl, etc.), piperidyl(lower)alkyl wherein piperidyl is optionally substituted with lower alkyl (e.g. piperidylmethyl, piperidylethyl, piperidylpropyl, ethylpiperidylethyl, ethylpiperidylhexyl, etc.), thiomorpholinyl(lower)alkyl (e.g., thiomorpholinylmethyl, thiomorpholinylethyl, thiomorpholinylpropyl, etc.), pyrrolidinyl(lower)alkyl wherein pyrrolidinyl is optionally substituted with lower alkyl (e.g., pyrrolidinylmethyl, pyrrolidinylethyl, N-ethylpyrrolidinylmethyl, methylpyrrolidinylpropyl, isopropylpyrrolidinylhexyl, etc.), and the like.

Suitable "N-containing heterocyclic group which is formed by conjugation of $R^7$, $R^8$ and the adjacent nitrogen atom" may include unsaturated 5- or 6-membered heteromonocyclic group containing 1 or 2 nitrogen atom(s), for examples, 1-pyrrolyl, 1-imidazolyl, 1-pyrazolyl, pyridinio, pyrimidinio, 1,2,3,6-tetrahydropyridin-1-yl, etc.; saturated 5-, 6- or 7-membered heteromonocyclic group containing 1 or 2 nitrogen atom(s) and/or 1 or 2 oxygen atom(s), for example, 1-pyrrolidinyl, 1-imidazolidinyl, piperidino, 1-piperazinyl, 1-homopiperazinyl, morpholino, etc.; saturated aza- or diaza-bicyclo hydrocarbon group such as 6-5 ring system (e.g., 1,4-diazabicyclo[4.3.0]nonan4-yl, 2,5-diazabicyclo[4.3.0]nonan-2-yl, 3-azabicyclo[4.3.0]nonan-3-yl, etc.), 6-6 ring system (e.g., 1,4-diazabicyclo[4.4.0]decan-4-yl, etc.), etc., saturated 5- or 6-membered heteromonocyclic group containing 1 or 2 nitrogen atom(s) and 1 or 2 sulfur atom(s), for example, 3-thiazolidinyl, thiomorpholino, etc., or phthalimido and the like.

Said "N-containing heterocyclic group formed by conjugation of $R^7$, $R^8$ and the adjacent nitrogen atom" may have 1 to 3 substituent(s) selected from the group consisting of hydroxy, lower alkyl, lower alkoxy, mono- or di-(lower)alkylamino(lower)alkyl, hydroxy(lower)alkyl, esterified carboxy(lower)alkyl, cyclo(lower)alkyl(lower)alkyl, acyl, acyl(lower)alkyl, phenylsulfonyl optionally substituted with halogen, phenyl(lower)alkenyl and a group of the formula:

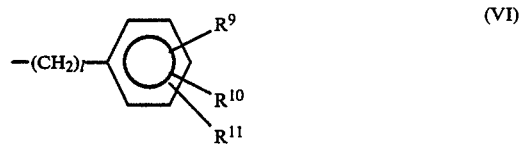

(VI)

(in which l is as defined above and $R^9$, $R^{10}$ and $R^{11}$ are each hydrogen or lower alkoxy)

Suitable "mono- or di-(lower)alkylamino" moiety, "lower alkyl" moiety and "esterified carboxy" moiety in the mono- or di-(lower)alkylamino(lower)alkyl and esterified carboxy(lower)alkyl groups are the same as exemplified above.

More preferable "mono- or di-(lower)alkylamino(lower)alkyl" may include methylaminomethyl, dimethylaminomethyl, ethylaminomethyl, diethylaminomethyl, N-methyl-N-ethylaminomethyl, dimethylaminoethyl, diethylaminoethyl, propylaminomethyl, isopropylaminoethyl and the like.

More preferable "esterified carboxy(lower)alkyl" may include methoxycarbonylmethyl, methoxycarbonylethyl, ethoxycarbonylmethyl, ethoxycarbonylethyl and the like.

Suitable "cyclo(lower)alkyl(lower)alkyl" may include cyclopropylmethyl, 2-cyclopropylethyl, 3-cyclopropylpropyl, 2-cyclopropylbutyl, 5-cyclopropylpentyl, 6-cyclopropylhexyl, cyclobutylmethyl, 2-cyclopentylethyl, cyclohexylmethyl, and the like.

Suitable "acyl" and "acyl" moiety in the "acyl(lower)alkyl" may include lower alkanoyl as exemplified above, lower alkylcarbamoyl (e.g., methylcarbamoyl, ethylcarbamoyl, isopropylcarbamoyl, t-butylcarbamoyl, pentylcarbamoyl, hexylcarbamoyl, etc.), aroyl (e.g., benzoyl, naphthoyl, etc.), furoyl, thenoyl, and the like.

Preferable examples of "acyl(lower)alkyl" may include lower alkylcarbamoyl(lower)alkyl such as methylcarbamoylmethyl, isopropylcarbamoylmethyl and the like.

Suitable "phenylsulfonyl optionally substituted with halogen" may include phenylsulfonyl, chlorophenylsulfonyl, bromophenylsulfonyl, fluorophenylsulfonyl, dichlorophenylsulfonyl and the like.

Suitable "phenyl(lower)alkenyl" may include styryl, cinnamyl and the like.

Suitable groups of the formula:

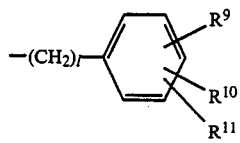
(VI)

(in which l, $R^9$, $R^{10}$ and $R^{11}$ are each as defined above) may include phenyl, methoxyphenyl, dimethoxyphenyl, trimethoxyphenyl, ethoxyphenyl, benzyl, methoxybenzyl, dimethoxybenzyl, trimethoxybenzyl, diethoxybenzyl and the like.

Suitable "lower alkylene" may include straight or branched one such as methylene, ethylene, methylmethylene, methylethylene, trimethylene, pentamethylene, hexamethylene, ethylethylene, propylene and the like.

The "lower alkylene" may be substituted with a lower alkylidene such as methylene, ethylidene, propylidene, butylidene and the like. Suitable "lower alkylene group substituted with a lower alkylidene" may incude methylenethylene, ethylidenethylene, methylenepropylene and the like.

Suitable pharmaceutically acceptable salts of the object compound (I) are conventional non-toxic salts and may include a salt with an organic or inorganic acid such as maleic acid, fumaric acid, tartaric acid, citric acid, acetic acid, benzoic acid, hydrochloric acid, sulfuric acid, nitric acid, hydroiodic acid, phosphoric acid and the like.

The object compound (I) of the present invention can be prepared by the following Processes.

Process 1

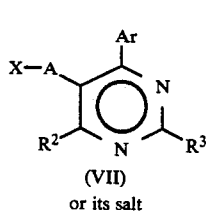
(VII) or its salt

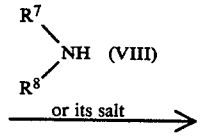
(VIII) or its salt

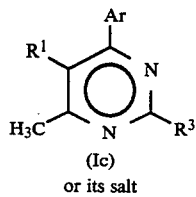
(Ia) or its salt

Process 2

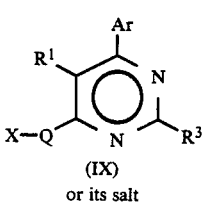
(IX) or its salt

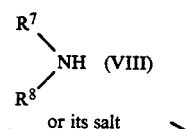
(VIII) or its salt

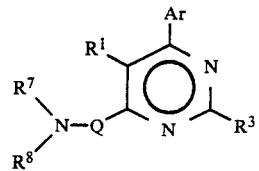
(Ib) or its salt

Process 3

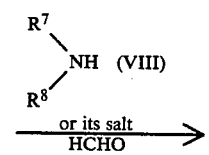
(Ic) or its salt

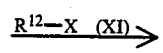
(VIII) or its salt / HCHO

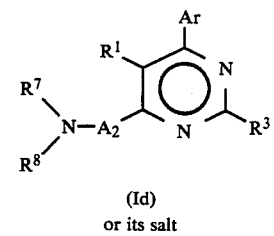
(Id) or its salt

Process 4

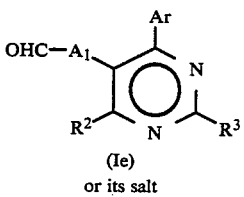
(Ie) or its salt (i) 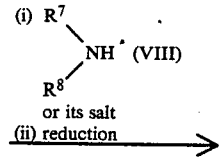 (VIII) or its salt
(ii) reduction

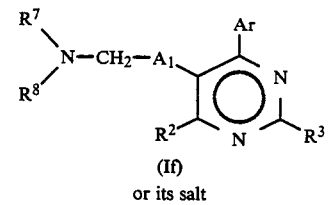
(If) or its salt

Process 5

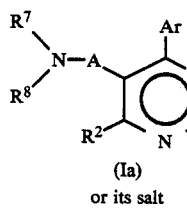

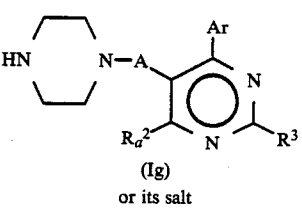
(Ig) or its salt $R^{12}—X$ (XI)

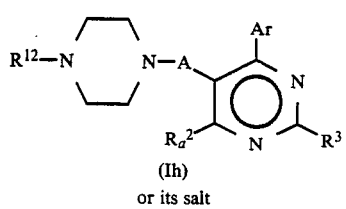
(Ih) or its salt

-continued

Process 6

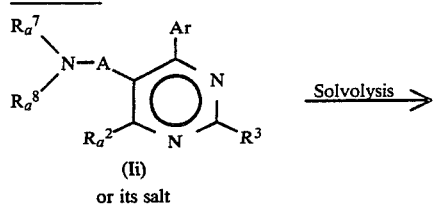

(Ii)
or its salt

Solvolysis →

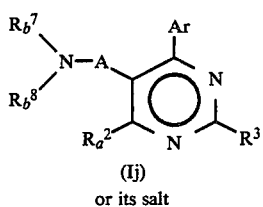

(Ij)
or its salt

Process 7

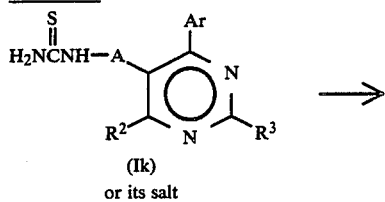

(Ik)
or its salt

→

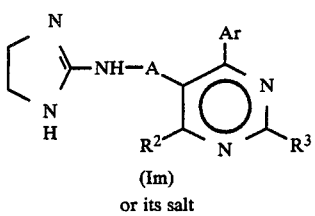

(Im)
or its salt

Process 8

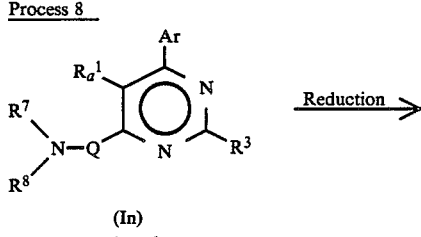

(In)
or its salt

Reduction →

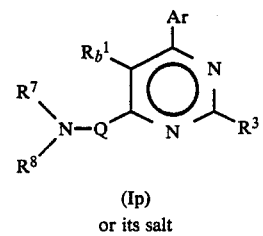

(Ip)
or its salt wherein,
Ar, $R^1$, $R^2$, $R^3$, $R^7$, $R^8$, A and Q are each as defined above,
$R_a^1$ is lower alkanoyl group or esterified carboxy group,
$R_b^1$ is hydroxy(lower)alkyl group,
$R_a^2$ is hydrogen or lower alkyl group,
$R_a^7$ and $R_a^8$ and are taken together to form a phthalimido or 4-(lower alkanoyl)piperazin-1-yl, $R_a^7$ and $R_b^8$ are both hydrogens or taken together to form a piperazin-1-yl,
$R^{12}$ is lower alkyl, hydroxy(lower)alkyl, cyclo(lower)alkyl(lower)alkyl, acyl, acyl(lower)alkyl, phenylsulfonyl optionally substituted with halogen or a group of the formula:

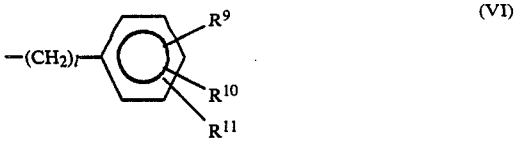

(VI)

l is as defined above,
$R^9$, $R^{10}$ and $R^{11}$ are each hydrogen or lower alkoxy,
$A_1$ is valency bond or lower alkylene group,
$A_2$ is ethylene group or methylenethylene group and
X is acid residue.

Each definitions in the above are the same as exemplified before.

Preferable examples of "acid residue" may include halogen as mentioned above, acyloxy (e.g., mesyloxy, benzenesulfonyloxy, tosyloxy, etc.) and the like.

The methods for preparing the object compounds (I) of the present invention are explained in more details in the following.

Process 1

The compound (Ia) and its salt can be prepared by reacting a compound (VII) or its salt with a compound (VIII) or its salt.

Suitable salt of the compounds (VII) and (VIII) are the same as the ones exemplified for the compound (I).

This reaction can be conducted in a conventional manner of amination of halogenated hydrocarbon.

This reaction is typically carried out in a conventional solvent such as water, methanol, ethanol, isopropyl alcohol, dioxane, tetrahydrofuran, N-N-dimethylformamide, methylene chloride, chloroform or any other organic solvent which does not adversely influence the reaction.

The reaction temperature is not critical and the reaction can be carried out under cooling to heating.

This reaction can also be conducted in the presence of an inorganic base such as an alkali metal hydride [e.g. sodium hydride, potassium hydride, etc.], an alkaline earth metal hydride [e.g. calcium hydride, magnesium hydride, etc.], an alkali metal hydroxide [e.g. sodium hydroxide, potassium hydroxide, etc.], an alkali metal carbonate or bicarbonate [e.g. sodium carbonate, potassium carbonate, sodium bicarbonate, potassium bicarbonate, etc.], or an organic base such as tert-amines [e.g., triethylamine, pyridine, N-N-dimethylaniline, etc.] or the like.

The present reaction can also be conducted in the presence of alkali metal halide [e.g., sodium iodide, potassium iodide etc.] or the like.

Process 2

The compound (Ib) and its salt can be prepared by reacting a compound (IX) or its salt with a compound (VIII) or its salt.

Suitable salt of the compounds (VIII) and (IX) are the same as the ones exemplified for the compound (I).

The reaction can be carried out substantially in the same manner as that of Process 1. Accordingly, the reaction mode and conditions can be referred thereto.

Process 3

The compound (Id) and its salt can be prepared by reacting a compound (Ic) or its salt with formaldehyde and a compound (VIII) or its salt.

Suitable salt of the compound (VIII) is the same as the ones exemplified for the compound (I).

The reaction can be conducted in a similar manner to that of well-known Mannich Reaction.

This reaction is typically carried out in a solvent under warming or heating.

Suitable solvent may include alcohol (e.g., methanol, ethanol, isopropyl alcohol, etc.), acetic acid, halogenated hydrocarbon (e.g., dichloromethane, dichloroethane, chloroform, carbon tetrachloride, etc.), water, acetonitrile, ether (e.g., diethylether, dioxane, etc.), N,N-dimethylformamide, or any other solvent which does not adversely influence the reaction.

This reaction can preferably be conducted under an acidic condition by using acetic acid, hydrochloric acid, sulfuric acid, cationic ion exchange resin or the like

Process 4

The compound (If) and its salt can be prepared by reacting a compound (Ie) or its salt with a compound (VIII) or its salt and then reducing the resulting compound.

Suitable salt of the compound (VIII) is the same as the ones exemplified for the compound (I).

The first step reaction is usually carried out in a conventional solvent such as water, methanol, ethanol, propanol, tetralin, tetrahydrofuran, dioxan, chloroform, benzene, toluene, dimethylformamide, dimethylsulfoxide or any other organic solvent which does not adversely influence the reaction.

This reaction is preferably conducted in the presence of an acid such as inorganic acid [e.g. hydrochloric acid, sulfuric acid, polyphosphoric acid, etc.], organic acid [e.g. trifluoroacetic acid, benzenesulfonic acid, toluenesulfonic acid, etc.] or the like.

The reaction can also be conducted under dehydrating condition such as an azeotropic dehydration, in the presence of a dehydrating agent [e.g. magnesium sulfate, anhydrous zinc chloride, phosphorus pentoxide, zeolite, silica gel, etc.] or the like.

The reaction temperature is not critical, and the reaction is usually carried out at ambient temperature or under warming or heating.

The reduction in the second step can be carried out by a conventional method, for example, by chemical or catalytic reduction.

Preferred examples of reducing agents to be used in the chemical reduction are lithium aluminum hydride, diborane, sodium borohydride, boron-tetrahydrofuran and the like.

Preferred examples of catalysts to be used in the catalytic reduction are conventional ones such as platinum catalysts (e.g. platinum plate, spongy platinum, platinum black, colloidal platinum, platinum oxide, etc.), palladium catalysts (e.g. spongy palladium, palladium black, palladium oxide, palladium on carbon, colloidal palladium, etc.), or the like.

The reduction is usually carried out in a solvent such as water, alcohol (e.g. methanol, ethanol, etc.), tetrahydrofuran or the like, and preferably under somewhat milder conditions such as under cooling, at room temperature or under warming.

Process 5

The compound (Ih) and its salt can be prepared by reacting a compound (Ig) or its salt with a compound (XI).

This reaction is typically carried out in a conventional solvent such as acetonitrile, halogenated hydrocarbon as exemplified before, alcohol as exemplified before, or any other solvent which does not adversely influence the reaction, and preferably in the presence of an inorganic base or organic base as exemplified in Process 1, a salt of an organic acid (e.g., sodium acetate, etc.), or the like.

The reaction temperature is not critical and the reaction can be carried out under cooling to heating.

Process 6

The compound (Ij) and its salt can be prepared by subjecting a compound (Ii) or its salt to a solvolysis.

The solvolysis can be conducted by a conventional method such as hydrolysis, aminolysis, alcoholysis, or the like.

Among these methods, aminolysis and solvolysis are preferable.

The aminolysis is typically conducted in a conventional solvent (e.g., water, alcohol as exemplified before, halogenated hydrocarbon as exemplified before, or the like) by using hydrazine or ammonia or the like.

The hydrolysis is typically conducted in the presence of an acid (e.g. hydrochloric acid, sulfuric acid, acetic acid, trifluoroacetic acid, p-toluenesulfonic acid, etc.) or a base (e.g. sodium hydroxide, sodium ethoxide, triethylamine, etc.) in a solvent such as alcohol as exemplified before, benzene or any other solvents which do not adversely affect the reaction.

The reaction temperature is not critical and the reaction can be carried out at any temperature under cooling to heating.

Process 7

The compound (Im) and its salt can be prepared by reacting a compound (Ik) or its salt with a compound of the formula:

$$R^{13}\text{-}X \tag{XII}$$

(wherein, X is as defined above, and $R^{13}$ is lower alkyl group) and then reacting with ethylenediamine or its salt.

Suitable salts of the compound (XII) and ethylenediamine are the same as exemplified for the compound (I).

The first step reaction is usually carried out in a solvent such as methanol, ethanol or any other solvents which do not adversely affect the reaction.

The present reaction can be carried out in the presence of a base as aforementioned.

The reaction temperature is not critical and the reaction is preferably carried out at ambient temperature or under warming.

The obtained product can be reacted with ethylenediamine without isolation.

The reaction of the above obtained compound and ethylenediamine or its salt is usually carried out in a solvent such as methanol, ethanol or any other solvents which do not adversely affect the reaction.

The reaction temperature is not critical and the reaction is preferably carried out at ambient temperature or under warming.

Process 8

The compound (Ip) and its salt can be prepared by reducing a compound (In) or its salt.

The reduction can be conducted according to a similar manner to that of the abovementioned second step of Process 4.

The object compounds and their salts prepared in the above processes can be isolated from the reaction mixture and purified by a conventional manner.

All of the compounds (Ia) to (Ip) are included in the scope of the compound (I), and the salts of the compounds (Ia) to (Ip) are to be referred to the salts of the compound (I).

Some of the starting compounds used in the above processes are new and they can be prepared by the method of the following process A, Preparations 1 to 7 or chemically equivalent thereof.

Process A

Process A $$\underset{\text{(XIII) or its salt}}{\overset{Ar}{\underset{R_b{}^2}{\overset{R_c{}^1}{\bigcirc}}}\!\!\!\!\!\!\!\!\!\!\!\!\!\!\!\!\!\!\!{\underset{N}{\phantom{X}}}R^3} \xrightarrow{\text{halogenation}} \underset{\text{(XIV) or its salt}}{\overset{Ar}{\underset{Hal-Q\phantom{XX}N}{\overset{R_c{}^1}{\bigcirc}}}\!\!\!\!\!\!\!\!\!\!\!\!\!\!\!\!\!\!\!{\underset{N}{\phantom{X}}}R^3}$$

wherein

Ar, $R^3$, and Q are each as defined above,
$R_c{}^1$ is esterified carboxy group,
$R_b{}^2$ is lower alkyl and
Hal is halogen.

The method for preparing the starting compounds (XIV) of the present invention is explained in more details in the following.

Process A

The compound (XIV) and its salt can be prepared by reacting a compound (XIII) or its salt with a halogenating agent.

Suitable salts of the compounds (XIII) and (XIV) are the same as the ones exemplified for the compound (I).

Suitable examples of the halogenating agent to be used in this process may include a conventional ones such as phosphorus oxyhalide [e.g. phosphorus oxybromide, phosphorus oxychloride, etc.], phosphorus pentahalide [e.g. phosphorus pentabromide, phosphorus pentachloride, phosphorus pentafluoride, etc.], phosphorus trihalide [e.g. phosphorus tribromide, phosphorus trichloride, phosphorus trifluoride, etc.], thionyl halide [e.g. thionyl chloride, thionyl bromide, etc.], triphenylphosphine dihalide [e.g. triphenylphosphine dichloride, triphenylphosphine dibromide, etc.], or the like.

This reaction is usually carried out in a conventional solvent such as methylene chloride, chloroform, carbon tetrachloride, benzene, tetrahydrofuran, dimethylformamide, dimethyl sulfoxide or any other organic solvent which does not adversely influence the reaction. In case that the halogenating agent is liquid, it can be used as a solvent.

The reaction temperature is not critical, and the reaction can be carried out under cooling to heating.

And further, it is to be noted that the starting compounds (XIV) are also useful in the treatment of cerebrovascular disease.

The pyrimidine derivative (I) and their pharmaceutically acceptable salts have been found to be useful in the treatment of cerebrovascular diseases such as cerebral apoplexy (e.g. cerebral hemorrhage, cerebral infarction, transient cerebral ischemic attack) or the like. For the purpose of showing utility of the Compound (I), pharmacological test data thereof are illustrated in the following.

Test 1

Effect on lipid peroxide production in rat brain mitochondria

Method

Brain mitochondria from male Wistar rat was incubated with 100 $\mu$M ascorbic acid, 20 $\mu$M FeSO$_4$ and test drug for 1 hr at 37° C. Malondialdehyde formed in the incubation mixture was measured by the thiobarbituric acid method according to Shimada et al (Biochem. Biophys. Acta, 489; 163–172. 1977)

Test compound

Following test compounds were dissolved in water.

Examples 1 and 12-(2)

Examples 2-(25) and 9

| Compounds | Results Inhibition % | |
|---|---|---|
| | at $10^{-4}$ g/ml | at $10^{-5}$ g/ml |
| Examples 1, 12-(2) | 100.0** | 94** |
| Examples 2-(25), 9 | — | 91.1* |

*P < 0.05 compared with control
**P < 0.01

The compounds listed in the table inhibited significantly the malondialdehyde formation in rat brain mitochondria at the dose of $10^{-4}$ g/ml.

Test 2

Effect on survival time of mice subjected to anoxia (100% N₂)

Method

A pair of male ICR mice with the same age was maintained in a close glass chamber in which circulated a current of nitrogen gas, and measured survival time.

One mouse was pretreated intraperitoneally with the test compound, and another with the vehicle 30 min before the experiment.

Test compound

The compounds were dissolved in saline.

| | | Result | | | |
|---|---|---|---|---|---|
| | | | Survival time (sec) | | |
| Compounds | n | Control | 10 mg/kg | Control | 100 mg/kg |
| Examples 1, 12–(2) | 10 | 27.5 ± 1.3 | 34.0 ± 1.8** | 27.5 ± 1.1 | 42.0 ± 1.5** |
| Examples 2–(25), 9 | 10 | 27.0 ± 1.1 | 31.5 ± 1.1** | 27.8 ± 0.9 | 40.3 ± 1.6** |

**$P < 0.01$ compared with control

The object compound (I) and pharmaceutically acceptable salts of this invention can be used in a form of a conventional pharmaceutical preparation, for example, in solid, semisolid or liquid form, which contains an active substance of this invention in admixture with an orgainic or inorganic carrier or excipient suitable for external, enteral or parenteral applications. The active ingredient may be compounded, for example, with the usual non-toxic, pharmaceutically acceptable carriers for tablets, pellets, capsules, suppositiories, solutions, emulsions, suspensions, and any other form suitable for use. The carriers which can be used are water, glucose, lactose, gum acacia, gelatin, mannitol, starch paste, magnesium trisilicate, talc, corn starch, keratin, collidal silica, potato starch, urea and other carriers suitable for use in manufacturing preparations, in solid, semisolid, or liquid form, and in addition auxiliary, stabilizing thickening and coloring agents and perfumes may be used. The pharmaceutical compositions can also contain preservative or bacteriostatic agents to keep the active ingredient in the desired preparatins stable in activity. The active object compound is included in the pharmaceutical composition in the amount sufficient to produce the desired therapeutic effect upon the process of condition of diseases.

While a dosage or therapeutically effective amount of the object compound (I) of this invention varies according to the age and conditions of each individual patient to be treated, a daily dose of about 0.1–100 mg/kg of the active ingredient is generally given for treating diseases.

The following Preparations and Examples are given for the purpose of illustrating this invention.

Preparation 1

(1) To a solution of methyl 4-methyl-2-phenyl-6-(3-nitrophenyl)-1,6-dihydro-5-pyrimidinecarboxylate (475 g) in chloroform (5 l) was added activated manganese dioxide (1.9 kg) and the mixture was refluxed for two hours with stirring vigorously. After allowing to cool to room temperature, manganese dioxide was filtered off. The filtrate was evaporated in vacuo and the residual precipitate was recrystallized from diisopropyl ether (500 ml). The crystal was filtered off, washed with diisopropyl ether and dried in vacuo to give methyl 6-methyl-4-(3-nitrophenyl)-2-phenyl-5-pyrimidinecarboxylate (320 g).

mp: 128°–130° C.

IR (Nujol): 1725, 1590, 1270 cm$^{-1}$.

NMR (DMSO-d$_6$, δ): 2.63 (3H, s), 3.77 (3H, s), 7.4–8.7 (9H, m)

Mass: 349 (M+).

(2) To a suspension of lithium aluminum hydride (12.24 g) in a mixture of dry tetrahydrofuran (180 ml) and diethyl ether (360 ml) was dropwise added a solution of methyl 6-methyl-4-(3-nitrophenyl)-2-phenyl-5-pyrimidinecarboxylate (45 g) in dry tetrahydrofuran (180 ml) under cooling at $-50° \sim -40°$ C. The excess lithium aluminum hydride was decomposed by a careful addition to ice water. The separated organic layer was washed with 15% sulfuric acid (400 ml) and extracted with ethyl acetate (1 l). The organic layer was washed with saturated aqueous sodium bicarbonate and aqueous sodium chloride successively and concentrated in vacuo. The residue was recrystallized from diethyl ether to give 5-hydroxymethyl-6-methyl-2-phenyl-4-(3-nitrophenyl)pyrimidine (30 g).

mp: 177°–178° C.

IR (Nujol): 1590, 1360, 1025 cm$^{-1}$.

NMR (DMSO-d$_6$, δ): 2.77 (3H, s), 4.55 (2H, d, J=4 Hz), 5.50 (1H, t, J=4 Hz), 7.3–7.67 (3H, m), 7.80 (1H, dd, J=8 Hz, 8 Hz), 8.1–8.6 (4H, m), 8.67 (1H, dd, J=2 Hz, 2 Hz).

Mass: 321 (M+).

(3) To a solution of phosphorus tribromide (16.85 g) in a mixture of benzene (150 ml) and tetrahydrofuran (150 ml) was dropwise added a solution of 5-hydroxymethyl-6-methyl-2-phenyl-4-(3-nitrophenyl)pyrimidine (30 g) in tetrahydrofuran (150 ml) under cooling at 7°–10° C. After stirring for 4 hours at the same temperature, the reaction mixture was poured into ice-water (200 ml), adjusted to pH 9.5 with saturated potassium carbonate and extracted with ethyl acetate (300 ml). After filtering off an insolble material, the organic layer was washed with saturated aqueous sodium chloride, dried over magnesium sulfate and evaporated in vacuo. The residue was recrystallized from diethyl ether to give 5-bromomethyl-6-methyl-2-phenyl-4-(3-nitrophenyl)pyrimidine (29.08 g).

mp: 163°–164° C.

IR (Nujol): 1550, 1530, 1350 cm$^{-}$.

NMR (CDCl$_3$, δ): 2.80 (3H, s), 4.47 (2H, s), 7.35–7.55 (3H, m), 7.73 (1H, dd, J=8 Hz, 8 Hz), 8.17 (1H, ddd, J=8 Hz, 2 Hz, 2 Hz), 8.3–8.6 (4H, m), 8.80 (1H, dd, J=2 Hz, 2 Hz)

Mass: 383, 385 (M+).

Preparation 2

(1) A mixture of 3-nitrobenzaldehyde (20 g), acetylacetone (13.25 g), acetic acid (1.58 g), and piperidine (0.45 g) in benzene (20 ml) was refluxed for 1 hour under azeotropic dehydration. To the reaction mixture was added diethyl ether (100 ml). The mixture was washed with water (50 ml) and a saturated aqueous solution of sodium chloride (50 ml) successively, dried over magnesium sulfate, and evaporated in vacuo. The residual substance was recrystallized from ether to afford 1-acetyl-1-(3-nitrobenzyliden)acetone(16.5 g).

mp: 92°–95° C.,

IR (Nujol): 1705, 1665, 1620, 915, 810 cm$^{-1}$,

NMR (DMSO-d$_6$, δ): 2.25 (3H, s), 2.47 (3H, s), 7.5–8.0 (3H, m), 8.1–8.5 (2H, m).

(2) A mixture of 1-acetyl-1-(3-nitrobenzyliden)acetone (10 g), benzamidine hydrochloride (8.06 g) and triethylamine (8.4 ml) in n-butanol (100 ml) was refluxed for 2 hours. The reaction mixture was added ethyl acetate (100 ml), washed with water (100 ml) and 5% hydrochloric acid (100 ml) successively. The solvent was evaporated and the residue was stirred with ethyl acetate (100 ml) for 1 hour. The crystals were collected by filtration, added a mixture of chloroform (100 ml) and water (100 ml) and adjusted to pH 8.5 by saturated potassium carbonate. The organic layer was evaporated in vacuo to give 5-acetyl-4-methyl-6-(3-nitrophenyl)-2-phenyl-1,6-dihydropyrimidine (4.46 g).

mp: 154°–155° C.,

IR (Nujol): 1655, 1590, 1530, 1340, 1245 cm$^{-1}$.

NMR (DMSO-d$_6$, δ): 2.23 (3H, s), 2.50 (3H, s), 5.93 (1H, s), 7.3–8.2 (9H, m), 9.60 (1H, s).

Mass: 335 (M+).

(3) 5-Acetyl-6-methyl-4-(3-nitrophenyl)-2-phenylpyrimidine (1.25 g) was obtained from 5-acetyl-4-methyl-6-(3-nitrophenyl)-2-phenyl-1,6-dihydropyrimidine (3.43 g) according to a similar manner to that of Preparation 1-(1).

mp: 131°–132° C.

IR (Nujol): 1700, 1530, 1348, 1245 cm$^{-1}$.

NMR (DMSO-d$_6$, δ): 2.28 (3H, s), 2.60 (3H, s), 7.50–8.70 (9H, m).

Mass: 334 (M+1).

(4) A mixture of 5-acetyl-6-methyl-4-(3-nitrophenyl)-2-phenylpyrimidine (3 g) and sodium borohydride (0.34 g) in methanol (110 ml) was stirred at room temperature for 4 hours. The reaction mixture was evaporated in vacuo and the residue was poured into a mixture of ethyl acetate and water. The separated organic layer was dried over magnesium sulfate and evaporated in vacuo. The crystalline residue was recrystallized from a mixture of n-hexane and diethyl ether to give a 5-(1-hydroxyethyl)-6-methyl-4-(3-nitrophenyl)-2-phenylpyrimidine (2.3 g).

mp : 119°–121° C.

IR (Nujol): 3350, 1585, 1535, 1350 cm$^{-1}$.

NMR (CDCl$_3$,δ): 1.62 (3H, d, J=7 Hz), 1.96 (1H, br) 2.88 (3H, s), 5.11 (1H, q, J=7 Hz), 7.3–8.5 (9H, m).

Mass: 334 (M−1).

(5) A solution of 5-(1-hydroxyethyl)-6-methyl-4-(3-nitrophenyl)-2-phenylpyrimidine (1.8 g) in tetrahydrofuran (10 ml) was dropped to a solution of phosphorus tribromide (0.34 ml) in tetrahydrofuran (20 ml) under ice cooling. The reaction mixture was stirred for 5 hours at the same condition and poured into ice water and extracted with ethyl acetate. The organic layer was evaporated in vacuo. The residue was chromatographed on silicagel eluting with chloroform. The fractions containing the desired product were combined and evaporated in vacuo. The residue was crystallized from diisopropyl ether to afford 5-(1-bromoethyl)-6-methyl-4-(3-nitrophenyl)-2-phenylpyrimidine (0.3 g).

mp: 133°–134° C.

IR (Nujol): 1530, 1350 cm$^{-1}$,

NMR (CDCl$_3$, δ): 2.01 (3H, d, J=7 Hz), 2.98 (3H, s), 5.4 (1H, q, J=7 Hz), 7.3–8.2 (5H, m), 8.2–8.7 (4H, m).

Mass: 397 (M+), 399 .

Preparation 3

(1) A solution of ethyl 2-(3,4-dimethoxybenzoyl)-acetate (25.2 g) and N,N-dimethylformamide dimethyl acetal (17.9 g) in tetrahydrofuran (100 ml) was refluxed for 18 hours under stirring. The reaction mixture was evaporated in vacuo to give ethyl 2-(3,4-dimethoxybenzoyl)-2-(dimethylaminomethylene)acetate (31.09) as an oil.

NMR (DMSO-d$_6$, δ) : 1.95 (3H, t, J=7 Hz), 2.90 (6H, s), 3.79 (3H, s), 3.83 (3H, s), 3.92 (2H, q, J=7 Hz), 7.02 (1H, d, J=7 Hz), 7.30 (1H, d, J=2 Hz), 7.35 (1H, dd, J=2, 9 Hz), 7.64 (1H, s).

(2) A solution of ethyl 2-(3,4-dimethoxybenzoyl)-2-(dimethylaminomethylene)acetate (31 g), acetoamidine hydrochloride (13.3 g) and triethylamine (16.2 g) in ethanol (200 ml) was refluxed for 10 hours under stirring. The reaction mixture was evaporated in vacuo and the residue was dissolved in a mixture of ethyl acetate and water. The separatedorganic layer was washed with brine, dried over magnesium sulfate and evaporated in vacuo. The residue was crystallized from ethyl ether to give ethyl 2-methyl-4-(3,4-dimethoxyphenyl)-5-pyrimidinecarboxylate (14 g).

mp: 98°–100° C.

IR (Nujol): 1710, 1603, 1572, 1535, 1510 cm$^{-1}$.

NMR (DMSO-d$_6$, δ) : 1.17 (3H, t, J=7 Hz), 2.72 (3H, s), 3.87 (6H, s), 4.25 (2H, q, J=7 Hz), 6.92–7.33 (3H, m), 8.85 (1H, s).

(3) 4-(3,4-Dimethoxyphenyl)-5-hydroxymethyl-2methylpyrimidine (1.1 g) was obtained from ethyl 2-methyl-4-(3,4-dimethoxyphenyl)-5-pyrimidinecarboxylate (7.6 g) according to a similar manner to that of Preparation 2-(4).

NMR (DMSO-d$_6$, δ): 2.65 (3H, s), 4.17 (6H, s), 4.52 (2H, d, J=5 Hz), 5.47 (1H, t, J=5 Hz), 6.93–7.20 (3H, m), 8.70 (1H, s), (4) 5-Bromomethyl-4-(3,4-dimethoxyphenyl)-2methylpyrimidine (0.9 g) was obtained from 4-(3,4-dimethoxyphenyl)-5-hydroxymethyl-2-methylpyrimidine (1.0 g) according to a similar manner to that of Preparation 1-(3).

IR (Nujol): 1625, 1590, 1515 cm$^{-1}$. Mass: 322, 324 (M+).

Preparation 4

(1) 2-(4-Methylpiperazin-1-ylcarbonyl)-1-(3-nitrophenyl)-1-buten-3-one (17.4 g) was obtained from 3-nitrobenzaldehyde (10 g) and 1-acetoacetyl-4methylpiperazine (20.4 g) according to a similar manner to that of Preparation 2-(1).

IR (Nujol): 1630, 1530 cm$^{-1}$.

Mass: 317 (M+).

(2) A mixture of 2-(4-methylpiperazin-1-ylcarbonyl)-1-(3-nitrophenyl)-1-buten-3-one (20 g), benzamidine hydrochloride (9.9 g) and triethylamine (11.4 ml) in n-butanol (200 ml) was refluxed for 2 hours. After evaporating the solvent, the residue was dissolved in a suspension of water (200 ml) and chloroform (200 ml). The separated organic layer was washed with saturated aqueous sodium chloride and dried over magnesium sulfate. To this solution was added activated manganese dioxide (120 g) and the mixture was refluxed for 1 hour with stirring vigorously. After cooling to a room temperature, manganese dioxide was filtered off. The filtrate was evaporated in vacuo, and the residue was subjected to column chromatography on alumina (200 g) eluting with chloroform. The fractions containing the object compound were combined and concentrated under reduced pressure. The crystals were recrystallized from diethyl ether to give 6-methyl-5-(4-methylpiperazin-1-ylcarbonyl)-4-(3-nitrophenyl)-2-phenylpyrimidine.

mp: 153°-155° C.
IR (Nujol): 1634, 1530, 1345 cm$^{-1}$.

Preparation 5

The following compounds were obtained according to a similar manner to that of Preparation 1,2,3 or 4.

(1)    5-Bromomethyl-4-[2-(4-chlorobenzyloxy)-phenyl]2,6-dimethylpyrimidine
mp: 119°-121° C.
IR (Nujol): 1600, 1585, 1550, 1240, 1220 cm$^{-1}$.
NMR (CDCl$_3$, δ): 2.58 (3H, s), 2.7 (3H, s), 4.26 (2H, s), 4.97 (2H, s), 6.85-7.5 (8H, m).
Mass: 417 (M+).

(2)    5-Bromomethyl-6-methyl-4-(4-nitrophenyl)-2-phenylpyrimidine
IR (Nujol): 1545, 1515, 1415, 1350 cm$^{-1}$.
NMR (CDCl$_3$, δ): 2.78 (3H, s), 4.45 (2H, s), 7.35-7.6 (3H, m), 7.85-8.65 (6H, m).

(3)    5-Bromomethyl-6-methyl-4-(2-nitrophenyl)-2-phenylpyrimidine
IR (Nujol): 1545, 1530, 1395, 1360 cm$^{-1}$.
NMR (CDCl$_3$, δ): 2.78 (3H, s), 4.36 (2H, s), 7.25-7.9 (6H, m), 8.0-8.6 (3H, m).

(4)    5-Bromomethyl-4-(3-trifluoromethylphenyl)-6-methyl-2-phenylpyrimidine
IR (Nujol): 1610, 1545, 1330 cm$^{-1}$.
NMR (CDCl$_3$, δ): 3.16 (3H, s), 4.51 (2H, s), 7.35-8.9 (9H, m).

(5) 5-(Bromomethyl)-4-(4-nitrophenyl)-2-phenylpyrimidine
IR (Nujol): 1565, 1535, 1520, 1430, 1360 cm$^{-1}$.
NMR (CDCl$_3$, δ): 4.47 (2H, s), 7.3-8.72 (9H, m), 8.93 (1H, s), Preparation 6

To a solution of 5-hydroxymethyl-6-methyl-4-(3-nitrophenyl)-2-phenylpyrimidine (0.3 g) in ethyl acetate (10 ml) was added activated manganese dioxide (2.4 g) and the mixture was refluxed for 2 hours under stirring vigorously. After allowing to stand to room temperature, manganese dioxide was filtered off. The filtrate was evaporated in vacuo, and the residual precipitate was recrystallized from diethyl ether to give 5-formyl-6-methyl-4-(3-nitrophenyl)-2-phenylpyrimidine (0.15 g).
mp: 154°-155° C.
IR (Nujol): 1700, 1535 cm$^{-1}$.
NMR (CDCl$_3$, δ): 2.97 (3H, s), 7.5-8.8 (9H, m), 10.13 (1H, s).
Mass: 39 (M$^{30}$).

Preparation 7

A mixture of methyl 6-methyl-4-(3-nitrophenyl)-2-phenyl-5-pyrimidinecarboxylate (5 g), pyridinium bromide perbromide (5.6 g) and 25% hydrogen bromide-acetic acid (5 ml) in acetic acid (200 ml) was stirred for 2 hours at room temperature. The reaction mixture was poured into ice water (200 ml) and stirred for 10 minutes. The resulting precipitates were collected and dissolved in a mixture of chloroform (50 ml) and water (50 ml). The separated organic layer was washed with saturated aqueous sodium hydrogen carbonate and saturated aqueous sodium chloride successively, dried over magnesium sulfate. The solvent was evaporated in vacuo and the residual crystal was recrystallized from ethanol to give methyl 6-bromomethyl-4-(3-nitrophenyl)-2-phenyl-5-pyrimidinecarboxylate (4.07 g).
mp: 103°-104° C.
IR (Nujol) : 1730, 1525, 1352 cm$^{-1}$.
NMR (CDC$_3$, δ) : 3.83 (3H, s), 4.78 (2H, s), 7.4-7.6 (3H, m), 7.70 (1H, dd, J=8 Hz, 8 Hz), 8.05 (1H, ddd, J=8 Hz, 2 Hz, 2 Hz), 8.35 (1H, ddd, J=8 Hz, 2 Hz, 2 Hz), 8.45-8.7 (3H, m).
Mass: 427, 429 (M+).

Example 1

A mixture of 5-bromomethyl-6-methyl-4-(3-nitrophenyl)-2-phenylpyrimidine (1.5 g), N-methylpiperazine (1.17 g) in isopropyl alcohol (15 ml) was refluxed for 6 hours. After evaporating the solvent, the residue was dissolved in chloroform, washed with saturated aqueous sodium chloride and dried over magnesium sulfate. The filtrate was evaporated under reduced pressure, and the residue was subjected to column chromatography on alumina (100 g) eluting with chloroform. The fractions containing the object compound were combined and concentrated under reduced pressure. The residue was recrystallized from diethyl ether to give 6-methyl-5-(4-methylpiperazin-1-ylmethyl)-4-(3-nitrophenyl)-2-phenylpyrimidine. (0.30 g).
mp: 138°-140° C.
IR (Nujol): 1525, 1348 cm$^{-1}$.
NMR (CDCl$_3$, δ): 2.27 (3H, s), 3.50 (2H, s), 8.8-9.0 (1H, m), 2.43 (8H, s), 7.3-7.8 (4H, m), 2.77 (3H, s), 8.0-8.6 (4H, m).
Mass: 403 (M+).

Example 2

The following compounds were obtained by reacting 5-bromomethyl-6-methyl-4-(substituted phenyl)-2-phenylpyrimidine with corresponding amine compounds according to a similar manner to that of Example 1.

(1) 6-Methyl-4-(3-nitrophenyl)-5-phthalimidomethyl-2-phenylpyrimidine
mp: 194°-195° C.
IR (Nujol): 1775, 1705 cm$^{-1}$.
NMR (CDCl$_3$, δ): 2.70 (3H, s), 4.93 (2H, s), 7.7 (4H, s), 7.25-8.7 (9H, m).
Mass: 450 (M+).

(2)    5-(Diethylaminomethyl)-6-methyl-4-(3-nitrophenyl)-2-phenylpyrimidine
mp: 101°-103° C.
IR (Nujol: 1530, 1200 cm$^{-1}$.
NMR (CDCl$_3$, δ): 0.83 (6H, t, J=8 Hz), 2.30 (4H, q, J=8 HZ), 3.58 (2H, s) 7.5-8.7 (9H, m).
Mass: 376 (M+).

(3) 6-Methyl-5-[4-2-hydroxyethyl) piperazin-1-ylmethyl]-4-(3-nitrophenyl)-2-phenylpyrimidine
mp: 89° C.
IR (Nujol: 1610, 1580, 1530, 1435, 1355 cm$^{-1}$.
NMR (CDCl$_3$, δ): 2.48 (8H, s), 252 (2H, t, J=6 HZ), 3.51 (2H, s), 3.58 (2H, dt, J=6 Hz), 7.33-9.0 (9H, m).
Mass: 433 (M+).

6-Methyl-5-(4-methylhomopiperazin-1-ylmethyl)-4-(3-nitrophenyl)-2-phenylpyrimidine dihydrochloride
fusing point: 170° C.
clarified point: 180° C.

NMR (DMSOd$_6$, δ): 1.7–4.0 (10H, M), 2.67 (3H, s), 2.97 (3H, s), 4.45 (2H, br s) 7.4–8.75 (9H, m).
Mass: 417 (M+).
6-Methyl-5- [(6-R,S)-1,4-diazabicyclo[4.3.0]-nonan-4-ylmethyl[-4-(3-nitropheyl)-2-phenylpyrimidine
mp: 64°–68° C.
Ir (Nujol): 1525, 1350 cm$^{-1}$.
NMR (CdCl$_3$, δ): 1.0–3.4 (13H, m), 2.78 (3H, s), 3.55 (2H, s), 7.2–7.8 (4H, m), 7.9–8.7 (4H, m), 8.8–9.05 (1H, m).
mass: 429 (M+).

(6) 6-Methyl-5-[4-(2-methoxyphenyl)piperazin-1-ylmethyl]-4-(3-nitrophenyl)-2-phenylpyrimidine
mp: 177.5°–179° C.
IR (Nujol): 1530, 1500, 1350 cm$^{-1}$.
NMR (CDCl$_3$, δ): 2.4–2.9 (4H, m), 2.82 (3H, s), 2.85–3.23 (4H, m), 3.59 (2H, s), 3.85 (3H, s), 6.92 (4H, s), 7.3–7.83 (4H, m), 8.0–8.7 (4H, m), 8.9–9.1 (1H, m).
Mass: 495 (M+).
Elemental analysis: C$_{29}$H$_{29}$N$_5$O$_3$·¾H$_2$O: Calcd.: C 68.42, H 6.04, N 13.75. Found: C 68.33, H 6.29, N 13.75.

(7) 6Methyl-5-[4-(3,4,5-trimethoxybenzyl)piperazin-1-ylmethyl]-4-(3-nitrophenyl)-2-phenylpyrimidine dihydrochloride
mp: 216° C. (dec.).
IR (Nujol): 1590, 1530, 1510, 1430, 1350 cm$^{-1}$.
NMR (DMSO-d$_6$, δ): 2.6–3.3 (4H, m), 2.81 (3H, s), 3.66 (3H, s), 3.75–4.2 (4H, m), 3.77 (8H, s), 4.17 (2H, s), 7.0 (2H, s), 7.4–7.63 (3H, m), 7.7–7.94 (1H, m), 8.03–8.72 (5H, m)
Mass: 570 (M+1).

(8) 5-(4-Isopropylcarbamoylmethylpiperazin-1-ylmethyl)-6-methyl-4-(3-nitrophenyl)-2-phenylpyrimidine
mp: 172°–173° C.
IR (Nujol): 3490, 1665 cm$^{-1}$.
NMR (CDCl$_3$, δ): 1.15 (6H, d, J=7 Hz), 2.46 (8H, s), 2.78 (3H, s), 2.94 (2H, s), 3.54 (2H, s), 4.08 (1H, m), 6.85 (1H, br s), 7.35–7.60 (3H, m), 7.67 (1H, dd, J=8 Hz , 8 Hz), 8.11 (1H, ddd, J=8 Hz, 2 Hz, 2 Hz), 8.34 (1H, ddd, J=8 Hz, 2 Hz, 2 Hz), 8.5–8.7 (2H, m), 8.88 (1H, dd, J=2 Hz, 2 Hz).
Mass: 488 (M+).

(9) 6-Methyl-5-[N-methyl-N-(2,2-dimethylaminoethyl)aminomethyl]-4-(3-nitrophenyl)-2-phenylpyrimidine dihydrochloride
mp: 214°–216° C. (dec.).
IR (Nujol): 1545, 1530, 1400, 1350 cm$^{-1}$.
NMR (DMSO-d$_6$, δ): 2.32 (3H, s), 2.7 (6H, s), 2.92 (3H, s), 3.1–3.7 (4H, m), 4.3 (2H, br s), 7.4–8.6 (9H, m).
Mass: 405 (M+).

(10) 6-Methyl-5-[N-(2-morpholinoethyl)aminomethyl]-4-(3-nitrophenyl)-2-phenylpyrimidine
mp: 110°–114° C.
IR (Nujol): 1580, 1535, 1400, 1350 cm$^{-1}$.
NMR (CDCl$_3$, δ): 2.3–2.95 (8H, m), 2.79 (3H, s), 3.55–3.8 (4H, m), 3.76 (2H, s), 7.33–7.8 (4H, m), 8.2–8.6 (4H, m), 9.07 (1H, dd, J=2 Hz, 2 Hz).
Mass: 434 (M+1).
Elemental analysis: C$_{24}$H$_{27}$N$_5$O$_3$: Calcd.: C 66.50, H 6.28, N 16.15. Found: C 66.53, H 6.10, N 16.19.

(11) 5-[N-(l-Ethylpyrrolidin-2-ylmethyl)aminomethyl]-6-methyl-4-(3-nitrophenyl)-2-phenylpyrimidine
mp: 91°–94° C.
IR (Nujol): 1535, 1400, 1350 cm$^{-1}$.
NMR (CDCl$_3$, δ): 1.11 (3H, t, J=7 Hz), 1.3–3.3 (11H, m), 2.78 (3H, s), 3.74 (2H, s), 7.3–7.83 (4H, m), 8.2–8.64 (4H, m), 8.93–9.12 (1H, m).
Mass: 432 (M+1).

Elemental analysis: C$_{25}$H$_{29}$N$_5$O$_2$: Calcd. C 69.58, H 6.77, N 16.23, Found C 69.56, H 6.47, N 16.06.

(12) 5-[N-(l-Ethylpiperidin-3-yl)aminomethyl]-6-methyl-4-(3-nitrophenyl)-2-phenylpyrimidine dihydrochloride
mp: 267° C. (dec.).
IR (Nujol): 1575, 1535, 1400, 1360 cm$^{-1}$.
NMR (CF$_3$COOD, δ): 1.44 (3H, t, J=7 Hz), 1.65–2.55 (4H, m), 2.8–4.5 (7H, m), 3.38 (3H, s), 5.23 (2H, s), 7.5–9 (9H, m).
Mass: 431 (M+).

(13) 5-[2-(Diethylaminomethyl)imidazol-1-ylmethyl]-6-methyl-4-(3-nitrophenyl)-2-phenylpyrimidine
mp: 107°–109° C.
IR (Nujol): 1580, 1545, 1530, 1350 cm$^{-1}$.
NMR (CDCl$_3$, δ): 0.95 (6H, t, J=7 Hz), 2.5 (4H, q, J=7 Hz), 2.58 (3H, s), 3.62 (2H, s), 5.3 (2H, s), 6.57 (1H, d, J=2 Hz), 6.95 (1H, d, J=2 Hz), 7.4–7.85 (5H, m), 8.2–8.7 (4H, m).
Mass: 456 (M+).

(14) 6-Methyl-4-(3-nitrophenyl)-2-phenyl-5-(piperidinomethyl)pyrimidine
mp: 140°–141° C.
IR (Nujol): 1590, 1530, 1350 cm$^{-1}$.
NMR (CDCl$_3$, δ): 1.2–1.6 (6H, m), 2.15–2.4 (4H, m), 2.75 (3H, s), 3.41 (2H, s), 7.35–7.50 (3H, m), 7.62 (1H, dd, J=8 Hz, 8 Hz), 8.11 (1H, ddd, J=8 Hz, 2 Hz, 2 Hz), 8.21 (1H, ddd, J=8 Hz, 2 Hz, 2 Hz), 8.40–8.60 (2H, m), 8.91 (1H, dd, J=2 Hz, 2 Hz).
Mass: 388 (M+).

(15) 6-Methyl-5-(4-hydroxypiperidinomethyl)-4-(3-nitrophenyl)-2-phenylpyrimidine
mp: 154°–164° C.
IR (Nujol): 1535, 1520, 1345 cm$^{-1}$.
NMR (CDCl$_3$, δ): 1.15–2.8 (8H, m), 2.79 (3H, s), 3.51 (2H, s), 3.53–3.9 (1H, m), 7.35–7.85 (4H, m), 8.03–8.7 (4H, m), 8.84–9.04 (1H, m).
Mass: 404 (M+).

(16) 6-Methyl-5-(4-cyclopropylmethylpiperazin-1-ylmethyl)-4-(3-nitrophenyl)-2-phenylpyrimidine
mp: 180° C.
IR (Nujol): 1530, 1350, 1300 cm$^{-1}$.
NMR (CDCl$_3$, δ): 0.1–0.34 (2H, m), 0.45–0.75 (2H, m), 0.8–1.37 (1H, m), 2.3–3.2 (8H, m), 2.51 (2H, d, J=6 Hz), 2.78 (3H, s), 3.58 (2H, s), 7.35–7.86 (4H, m), 7.95–8.66 (4H, m), 8.9–9.15 (1H, m).
Mass: 443 (M+).

(17) 6-Methyl-4-(3-nitrophenyl)-2-phenyl-5-thiomorpholinomethylpyrimidine
mp: 162°–164° C.
IR (Nujol): 1525, 1350 cm$^{-1}$.
NMR (CDCl$_3$, δ): 2.63 (8H, s), 2.77 (3H, s), 3.55 (2H, s), 7.4–7.56 (3H, m), 7.69 (1H, dd, J=7 Hz), 8.12 (1H, ddd, J=2, 2, 7 Hz), 8.2–8.6 (3H, m), 8.85 (1H, dd, J=2,2 Hz).

(18) 6-Methyl-5-(4-methylpiperazin-1-ylmethyl)-4-(4-nitrophenyl)-2-phenylpyrimidine
mp: 138°–142° C.
IR (Nujol): 1605, 1540, 1525, 1495, 1410, 1350 cm$^{-1}$.
NMR (CDCl$_3$, δ): 2.27 (3H, s), 2.38 (8H, s), 2.80 (3H, s), 3.53 (2H, s), 7.3–8.7 (9H, m).
Mass: 403 (M+).

(19) 6-Methyl-5-(4-methylpiperazin-1-ylmethyl)-4-(2-nitrophenyl)-2-phenylpyrimidine
mp: 117°–119° C.
IR (Nujol): 1545, 1530, 1350, 1300 cm$^{-1}$.
NMR (CDCl$_3$, δ): 2.22 (3H, s), 2.24 (8H, s), 3.27 (2H, s), 7.32–7.85 (6H, m), 8.13–8.57 (3H, m).

(20) 6-Methyl-5-(4-methylpiperazin-1-ylmethyl)-4-(3-trifluoromethylphenyl)-2-phenylpyrimidine
mp: 159°–162° C.
IR (Nujol): 1545, 1330, 1320 cm$^{-1}$.
NMR (CDCl$_3$, δ): 2.26 (3H, s), 2.39 (8H, s), 2.76 (3H, s), 3.5 (2H, s), 7.35–8.0 (6H, m), 8.21 (1H, br s), 8.37–8.64 (2H, m).
Mass: 426 (M+).

(21) 6-Methyl-5-[N-(2-pyrrolidin-1-ylethyl)aminomethyl]-4-(3-nitrophenyl)-2-phenylpyrimidine
fusing point: 60° C.
clarified point: 70° C.
IR (Nujol): 1545, 1535, 1400, 1350 cm$^{-1}$.
NMR (CDCl$_3$, δ): 1.6–1.9 (4H, m), 2.3–2.95 (8H, m), 2.78 (3H, s), 3.77 (2H, s), 7.33–7.8 (4H, m), 8.2–8.63 (4H, m), 8.97–9.14 (1H, m).
Mass: 417 (M+).

(22) 4-[2-(4-Chlorobenzyloxy)phenyl]-2,6-dimethyl-5-(4-methylpiperazin-1-ylmethyl)pyrimidine was prepared from 5-bromomethyl-4-[2-(4-chlorobenzyloxy)phenyl]-2,6-dimethylpyrimidine.
mp: 110°–111° C.
IR (Nujol): 1600, 1550, 1300 cm$^{-1}$.
NMR (CDCl$_3$, δ): 2.17 (11H, s), 2.63 (3H, s), 2.72 (3H, s), 3.2–3.36 (2H, m), 4.97 (2H, s), 6.9–7.5 (8H, m).
Mass: 436, 438 (M+).

(23) 5-(4-Methylpiperazin-1-ylmethyl)-4-(4-nitrophenyl)-2-phenylpyrimidine
mp: 194°–196° C.
IR (Nujol): 1565, 1535, 1520, 1425, 1350 cm$^{-1}$.
NMR (CDCl$_3$, δ): 2.3 (3H, s), 2.5 (8H, s), 3.48 (2H, s), 7.4–7.63 (3H, m), 8.22 (2H, d, J=9 Hz), 8.40 (2H, d, J=9 Hz), 8.37–8.67 (2H,m), 8.85 (1H,s).
Mass: 389 (M+).

(24) 4-(3,4-Dimethoxyphenyl)-2-methyl-5-(4-methylpiperazin-1-ylmethyl)pyrimidine
IR (Nujol): 1605, 1570, 1330, 1265 cm$^{-1}$.
NMR (CDCl$_3$, δ): 2.3 (3H, s), 2.49 (8H, s), 2.77 (3H, s), 3.45 (2H, s), 3.96 (6H, s), 6.95 (1H, d, J=8 Hz), 7.36–7.6 (2H, m), 8.61 (1H, s).
Mass: 342 (M+).

(25) 6-Methyl-5-[2-(N,N-dimethylamino)ethylaminomethyl]-4-(3-nitrophenyl)-2-phenylpyrimidine fumarate
mp: 104°–106° C.
IR (Nujol): 1705, 1530 cm$^{-1}$.

(26) 6-Methyl-5-[4-(2-furoyl)piperazin-1-ylmethyl]-4-(3-nitrophenyl)-2-phenylpyrimidine
IR (Nujol): 1630, 1530, 1350 cm$^{-1}$.
Mass: 483 (M+).

(27) 6-Methyl-5-[4-(4-fluorophenylsulfonyl)piperazin-1-ylmethyl]-4-(3-nitrophenyl)-2-phenylpyrimidine
IR (Nujol): 1595, 1525, 1495, 1355 cm$^{-1}$.
Mass: 547 (M+).

(28) 6-Methyl-5-(1-piperazinylmethyl)-4-(3-nitrophenyl)-2-phenylpyrimidine dihydrochloride
mp: 174° C. (dec.).
IR (Nujol): 1530, 1400, 1355 cm$^{-1}$.
Mass: 389 (M+).

(29) 5-Aminomethyl-6-methyl-4-(3-nitrophenyl)-2-phenylpyrimidine
mp: 145°–147° C.
IR (Nujol): 1545, 1520, 1360 cm$^{-1}$.
Mass: 320 (M+).

(30) 6-Methyl-5-(4-formylpiperazin-1-ylmethyl)-4-(3-nitrophenyl)-2-phenylpyrimidine hydrochloride
mp: 212°–214° C. (dec.).

IR (Nujol): 1675, 1545, 1525, 1350 cm$^{-1}$.
Mass: 417 (M+).

EXAMPLE 3

A mixture of 5-(1-bromoethyl)-6-methyl-4-(3-nitrophenyl)-2-phenylpyrimidine (1.5 g) and N-methylpiperazine (1.13 g) in isopropylalcohol (15 ml) was refluxed for 1.5 hours. The reaction mixture was evaporated in vacuo. The residue was chromatographed on allumina eluting with a mixture of ethyl acetate and n-hexane (1:20). The fractions containing the desired product were combined and concentrated in vacuo. The residue was crystallized from a mixture of n-hexane and diethyl ether to give 6-methyl-5-[1-(4-methylpiperazin-1-yl)ethyl]-4-(3-nitrophenyl)-2-phenylpyrimidine (0.51 g).
mp: 130°–131° C.
IR (Nujol): 1528, 1360 cm$^{-1}$.
NMR (CDCl$_3$, δ): 1.42 (3H, d, J=7 Hz), 2.27 (3H, s), 2.3–2.8 (8H, m), 2.94 (3H, s), 3.57 (1H, q, J=7 Hz), 7.4–7.9 (5H, m), 8.2–8.6 (4H, m).
Mass: 417 (M+).

EXAMPLE 4

(1) A mixture of ammonium thiocyanate (0.25 g) and benzoyl chloride (0.41 g) in acetone (20 ml) was refluxed for 2 hours, and 5-aminomethyl-6-methyl-4-(3-nitrophenyl)-2-phenylpyrimidine (0.9 g) in acetone (5 ml) was added thereto. After refluxing for 2 hours, the reaction mixture was poured into a mixture of chloroform (100 ml) and water (50 ml). The organic layer was separated, washed with saturated aqueous sodium chloride and dried over magnesium sulfate. The solvent was distilled off and the resulting crystal was recrystallized from diisopropyl ether to give 5-(3-benzoylthioureidomethyl)-6-methyl-4-(3-nitrophenyl)-2-phenylpyrimidine (1.1 g).
mp: 182°–187° C.
IR (Nujol): 1680, 1250 cm$^{-1}$.
NMR (CDCl$_3$, δ): 2.83 (3H, s), 4.91 (2H, d, J=5 Hz), 7.2–8.1 (10H, m), 8.2–8.6 (4H, m), 9.02 (1H, s), 10.85 (1H, br s).

(2) A mixture of 5-(3-benzoylthioureidomethyl)-6-methyl-4-(3-nitrophenyl)-2-phenylpyrimidine (1.0 g) and sodium hydroxide (0.089 g) in methanol (20 ml) and water (10 ml) was stirred for 1 hour at a room temperature. After evaporating the solvent, water (20 ml) was added thereto and stirred for 30 minutes. The resulting precipitates were collected by filtration, washed with water and dried over phosphorous pentoxide to give 6-methyl-4-(3-nitrophenyl)-2-phenyl-5-thioureidomethylpyrimidine (0.75 g).
mp: 227°–229° C.
IR (Nujol): 3380, 1630, 1530 cm$^{-1}$.

(3) A mixture of 6-methyl-4-(3-nitrophenyl)-2-phenyl-5-thioureidomethylpyrimidine (0.7 g) and methyl iodide (0.31 g) in N,N-dimethylformamide (20 ml) was stirred for 7 hours at a room temperature. After evaporating the solvent in vacuo, the residual product was dissolved in ethanol (14 ml). Ethylenediamine (0.33 g) was added thereto and refluxed for 2 hours. After cooling, the reaction mixture was poured into a mixture of chloroform (50 ml) and water (100 ml), and adjusted pH to 11.0 with 10% aqueous potassium carbonate. The organic layer was separated, washed with saturated aqueous sodium chloride, dried over magnesium sulfate, evaporated in vacuo. The residual product was subjected to column chromatography on alumina eluting with a mixture of chloroform and methanol (50:1). The fractions containing the object compound were combined and concentrated in vacuo. The residue was recrystallized from ethanol to give 5-(1-imidazolin-2-ylaminomethyl)-6-methyl-4-(3-nitrophenyl)-2-phenylpyrimidine (0.06 g).

mp: 220° C. (dec.).

IR (Nujol): 1530, 1350 cm$^{-1}$.

NMR (CDCl$_3$, $\delta$): 2.70 (3H, s), 3.48 (4H, s), 4.15 (2H, s), 7.3–7.8 (4H, m), 8.0–8.75 (5H, m).

Mass: 388 (M+).

EXAMPLE 5

To a suspension of methyl 6-bromomethyl-4-(3-nitrophenyl)-2-phenyl-5-pyrimidinecarboxylate (1.5 g) in isopropyl alcohol (15 ml) was added N-methylpiperazine (0.88 g) at 70° C. The reaction mixture was stirred for 10 minutes at the same temperature. After evaporating the solvent, the residue was dissolved in a mixture of chloroform (50 ml) and water (50 ml). The organic layer was separated, dried over magnesium sulfate and evaporated in vacuo. The residue was subjected to column chromatography on alumina (100 g) eluting with chloroform. The fractions containing the object compound were combined and concentrated under reduced pressure. The residual crystal was recrystallized from a mixture of diethyl ether and ethanol to give methyl 6-(4-methylpiperazin-1-ylmethyl)-4-(3-nitrophenyl)-2-phenyl-5-pyrimidinecarboxylate (0.37 g).

fusing point: 120° C.

clarified point: 126° C.

IR (Nujol): 1723, 1585, 1525, 1355 cm$^{-1}$.

NMR (CDCl$_3$, $\delta$): 2.27 (3H, s), 2.25–2.65 (8H, m), 3.83 (3H, s), 3.94 (2H, s), 7.4–7.6 (3H, m), 7.69 (1H, dd, J=8 Hz, 8 Hz), 8.12 (1H, ddd, J=8 Hz, 2 Hz, 2 Hz), 8.37 (1H, ddd, J=8 Hz, 2 Hz, 2 Hz), 8.45–8.75 (3H, m).

Mass: 447 (M+).

EXAMPLE 6

The following compounds were obtained from methyl 6-bromomethyl-4-(3-nitrophenyl)-2-phenyl-5-pyrimidinecarboxylate and corresponding amine compound according to a similar manner to that of Example 5.

(1) Methyl 6-morpholinomethyl-4-(3-nitrophenyl)-2-phenyl-5-pyrimidinecarboxylate mp: 125°–126° C.

IR (Nujol): 1718, 1585, 1530, 1350, 1265 cm$^{-1}$.

NMR (CDCl$_3$, $\delta$): 2.4–2.6 (4H, m), 3.5–3.75 (4H, m), 3.82 (3H, s), 3.93 (2H, s), 7.4–7.6 (3H, m), 7.67 (1H, dd, J=7, 7 Hz), 8.13 (1H, ddd, J=2, 2, 7 Hz), 8.39 (1H, ddd, J=2, 2, 7 Hz), 8.5–8.7 (3H, m).

Mass: 434 (M+).

(2) Methyl 6-diethylaminomethyl-4-(3-nitrophenyl)-2-phenyl-5-pyrimidinecarboxylate hydrochloride mp: 149° C. (dec.).

IR (Nujol): 1730, 1545, 1535, 1410, 1350 cm$^{-1}$.

NMR (CDCl$_3$, $\delta$): 1.58 (6H, t, J=8 Hz), 3.2–3.9 (4H, m), 3.81 (3H, s), 4.64 (2H, br s), 7.4–8.75 (9H, m).

Mass: 421 (M+1).

(3) Methyl 4-(3-nitrophenyl)-2-phenyl-6-phthalimidomethyl-5-pyrimidinecarboxylate mp: 176°–179° C.

IR (Nujol): 1770, 1735, 1710 cm$^{-1}$.

NMR (CDCl$_3$, $\delta$): 3.82 (3H, s), 5.30 (2H, s), 7.2–8.7 (13H, m).

EXAMPLE 7

A mixture of 5-acetyl-6-methyl-4-(3-nitrophenyl)-2-phenylpyrimidine (2.5 g), N-methylpiperazine dihydrochloride (1.3 g) and paraformaldehyde (95% pure 0.3 g) in acetic acid (15 ml) was refluxed for 6 hours. The reaction mixture was evaporated in vacuo and the residue was poured into a mixture of ethyl acetate and water. The mixture was acidified to pH 1.0 by 10% aqueous hydrochloric acid.

The aqueous layer was separated, adjusted to pH 9 by saturated potassium carbonate and extracted with chloroform. The extract was dried over magnesium sulfate and evaporated in vacuo. The residue was chromatographed on silicagel eluting with a mixture of chloroform and methanol (50:1). The fractions containing the desired product were combined and concentrated in vacuo. The resulting crystalline was recrystallized from diethyl ether to give 5-acetyl-6-[2-(4-methylpiperazin-1-yl)ethyl]-4-(3-nitrophenyl)-2-phenylpyrimidine (0.13 g).

mp: 88°–91° C.

IR (Nujol): 1685, 1530, 1350 cm$^{-1}$.

NMR (CDCl$_3$, $\delta$): 2.17 (3H, s), 2.30 (3H, s), 2.3–2.7 (8H, m), 3.0 (4H, s), 7.4–8.0 (5H, m), 8.2–8.8 (4H, m).

Mass: 445 (M+).

EXAMPLE 8

(1) Methyl 6-[2-(4-methylpiperazin-1-yl)ethyl]-4-(3-nitrophenyl)-2-phenyl-5-pyrimidinecarboxylate (0.15 g) was obtained from 6-methyl-4-(3-nitrophenyl)-2-phenyl-5-pyrimidinecarboxylate (3 g), 4-methylpiperazine dihydrochloride (1.49 g) and paraformaldehyde (0.33 g) according to a similar manner to that of Example 7.

mp: 99°–101° C.

IR (Nujol): 1720, 1530, 1350 cm$^{-1}$.

NMR (CDCl$_3$, $\delta$): 2.3 (3H, s), 2.4–2.8 (8H, m), 2.8–3.3 (4H, m), 7.4–7.6 (3H, m), 7.67 (1H, dd, J=8 Hz), 8.08 (1 H, ddd, J=8 Hz, 2 Hz, 2 Hz), 8.35 (1H, ddd, J=8 Hz, 2 Hz, 2 Hz), 8.4–8.7 (3H, m).

Mass: 461 (M+).

(2) Methyl 6-(2-dimethylaminoethyl)-4-(3-nitrophenyl)-2-phenyl-5-pyrimidinecarboxylate (0.95 g) was obtained from methyl 6-methyl-4-(3-nitrophenyl)-2-phenyl-5-pyrimidinecarboxylate (3 g), paraformaldehyde and dimethylamine hydrochloride (0.7 g) according to a similar manner to that of Example 7.

mp: 124°–126° C.

IR (Nujol): 1720, 1580, 1530, 1350 cm$^{-1}$.

NMR (CDCl$_3$, $\delta$): 2.35 (6H, s), 2.8–3.3 (4H, m), 3.8 (3H, s), 7.4–7.6 (3H, s), 7.65 (1H, dd, J=8 Hz), 8.09 (1H, ddd, J=8 Hz, 2 Hz, 2 Hz), 8.35 (1H, ddd, J=8 Hz, 2 Hz, 2 Hz), 8.45–8.7 (3H, m).

Mass: 406 (M+).

(3) 5-Acetyl-6-(2-dimethylaminoethyl)-4-(3-nitrophenyl)-2-phenylpyrimidine hydrochloride (0.7 g) was obtained from 5-acetyl-6-methyl-4-(3-nitrophenyl)-2-phenylpyrimidine (3 g), paraformaldehyde (0.36 g) and dimethylamine hydrochloride (0.73 g) according to a similar manner to that of Example 7.

mp: 138°–140° C.

IR (Nujol): 1690, 1530, 1355 cm$^{-1}$.

NMR (CDCl$_3$, $\delta$): 2.33 (3H, s), 2.93 (3H, s), 2.97 (3H, s), 3.4–3.9 (4H, m), 7.4–8.1 (5H, m), 8.23–8.80 (4H, m).

(4) 6-(2-Dimethylaminoethyl)-5-(4-methylpiperazin-1-ylcarbonyl)-4-(3-nitrophenyl)-2-phenylpyrimidine (0.45 g) [compound A]and 6-(2-dimethylamino-1-methylenethyl)-5-(4-methylpiperazin-1-ylcarbonyl)-

4-(3-nitrophenyl)-2-phenylpyrimidine (0.01 g) [compound B] were obtained from 6-methyl-5-(4-methyl-piperazin-1-ylcarbonyl)-4-(3-nitrophenyl)-2-phenyl-pyrimidine (3 g), paraformaldehyde (0.29 g) and dimethylamine hydrochloride (0.7 g) according to a similar manner to that of Example 7.

[compound A]

mp: 119°–120° C.

IR (Nujol): 1628, 1525, 1345 cm$^{-1}$.

NMR (CDCl$_3$, δ): 1.3–2.3 (4H, m), 2.13 (3H, s), 2.39 (6H, s), 3.02 (2H, t, J=3 Hz), 3.07 (2H, t, J=3 Hz), 2.75–3.2 (2H, m), 3.72 (2H, t, J=6 Hz), 7.4–7.8 (4H, m), 8.1–8.9 (5H, m).

Mass: 474 (M+).

[compound B]

NMR (CDCl$_3$, δ): 1.2–2.4 (4H, m), 2.1 (3H, s) 2.27 (6H, s), 2.7–4.0 (4H, m), 3.5 (2H, s), 5.6–5.8 (2H, m), 7.4–7.8 (4H, m), 8.2–8.9 (5H, m).

Mass: 486 (M+).

EXAMPLE 9

A mixture of 5-formyl-6-methyl-4-(3-nitrophenyl)-2-phenylpyrimidine (3 g), 2-dimethylaminoethylamine (0.83 g) and a catalytic amount of p-toluenesulfonic acid in benzene (30 ml) was refluxed for 2 hours under azeotropic dehydration. After removal of the solvent, the residue was dissolved with ethanol (30 ml), added sodium borohydride (360 mg) and stirred for 1 hour at room temperature. The reaction mixture was added in a suspension of chloroform (100 ml) and water (100 ml), adjusted to pH 8. The separated organic layer was washed with saturated aqueous sodium chloride, dried over magnesium sulfate and evaporated in vacuo. The residue was subjected to column chromatography on alumina (100 g) and eluted with chloroform. The fractions containing the object compound were combined and concentrated under reduced pressure. The residue and fumaric acid (0.4 g) were dissolved in ethanol (30 ml). The separated crystal was filtered and dried in vacuo to give 5-[N-(2-dimethylaminoethyl)aminomethyl]-6-methyl-4-(3-nitrophenyl)-2-phenylpyrimidine fumarate (0.69 g).

mp: 104°–106° C.

IR (Nujol): 1705, 1530 cm$^{-1}$.

NMR (DMSO-d$_6$, δ): 2.50 (6H, s), 2.76 (3H, s), 2.87 (4H, s), 3.67 (2H, s), 6.53 (2H, s), 7.3–7.6 (3H, m), 7.80 (1H, dd, J=8 Hz, 8 Hz), 8.2–8.5 (4H, m), 8.83 (1H, dd, J=2 Hz, 2 Hz).

EXAMPLE 10

The following compounds are obtained from 5-formyl-6-methyl-4-(3-nitrophenyl)-2-phenylpyrimidine and corresponding amine compounds.

(1) 6-Methyl-5-[N-(2-morpholinoethyl)aminomethyl]-4-(3-nitrophenyl)-2-phenylpyrimidine mp: 110°–114° C.

IR (Nujol): 1580, 1535, 1400, 1350 cm$^{-1}$.

Mass: 434 (M+1).

(2) 5-[N-(1-Ethylpyrrolidin-2-ylmethyl)aminoethyl]-6-methyl-4-(3-nitrophenyl)-2-phenylpyrimidine mp: 91°–94° C.

IR (Nujol): 1535, 1400, 1350 cm$^{-1}$.

Mass: 432 (M+1).

(3) 5-[N-(1-Ethylpiperidin-3-yl)aminomethyl]-6-methyl-4-(3-nitrophenyl)-2-phenylpyrimidine dihydrochloride mp: 267° C. (dec.)

IR (Nujol): 1575, 1535, 1400, 1360 cm$^{-1}$.

Mass: 431 (M+).

EXAMPLE 11

To a mixture of 6-methyl-5-(1-piperazinylmethyl)-4-(3-nitrophenyl)-2-phenylpyrimidine dihydrochloride (1 g), dichloromethane (10 ml) and triethylamine (0.48 g), was added 2-furoyl chloride (0.31 g) at 5° C. under ice cooling. After stirring for 1 hour at the same temperature, the reaction mixture was concentrated under reduced pressure. The residue was suspended in water and adjusted to pH=9 with aqueous saturated sodium hydrogen carbonate. The precipitate was collected by filtration, washed with water and dried in vacuo to give 6-methyl-5-[4-(2-furoyl)piperazin-1-ylmethyl]-4-(3-nitrophenyl)-2-phenylpyrimidine (1.02 g).

fusing point: 178° C.

clarified point: 188° C.

IR (Nujol): 1630, 1530, 1350 cm$^{-1}$.

NMR (DMSO-d$_6$, δ): 2.2–4.0 (8H, m), 2.83 (3H, s), 3.57 (2H, s), 6.6 (1H, dd, J=2 Hz, 3 Hz), 6.96 (1H, d, J=3 Hz), 7.35–8.8 (10H, m).

Mass: 483 (M+).

EXAMPLE 12

The following compounds were obtained according to a similar manner to that of Example 11.

(1) 6-Methyl-5-[4-(4-fluorophenylsulfonyl)piperazin-1-ylmethyl]-4-(3-nitrophenyl)-2-phenylpyrimidine (1.03 g) was obtained from 6-methyl-5-(piperazin-1-ylmethyl)-4-(3-nitrophenyl)-2-phenylpyrimidine dihydrochloride (1 g) and 4-fluorophenylsulfonyl chloride (0.46 g).

mp: 196°–220° C.

IR (Nujol): 1595, 1525, 1495, 1355 cm$^{-1}$.

NMR (CDCl$_3$, δ): 2.35–2.6 (4H, m), 2.72 (3H, s), 2.85–3.1 (4H, m), 3.54 (2H, s), 7.15–8.9 (13H, m).

Mass: 547 (M+).

(2) 6-Methyl-5-(4-methylpiperazin-1-ylmethyl)-4-3-nitrophenyl)-2-phenylpyrimidine is obtained from 6-methyl-5-(piperazin-1-ylmethyl)-4-(3-nitrophenyl)-2-phenylpyrimidine dihydrochloride and methyl iodide.

mp: 138°–140° C.

IR (Nujol): 1525, 1348 cm$^{-1}$.

Mass: 403 (M+).

(3) 6-Methyl-5-[4-(2-hydroxyethyl)piperazin-1-ylmethyl]-4-(3-nitrophenyl)-2-phenylpyrimidine mp: 89° C.

IR (Nujol): 1610, 1580, 1530, 1435, 1355 cm$^{-1}$.

Mass: 433 (M+).

(4) 6-Methyl-5-[1-(4-methylpiperazin-1-yl)ethyl]-4-(3-nitrophenyl)-2-phenylpyrimidine mp: 130°–131° C.

IR (Nujol): 1528, 1360 cm$^{-1}$.

Mass: 417 (M+).

(5) 6-Methyl-5-[4-(3,4,5-trimethoxybenzyl)piperazin-1-ylmethyl]-4-(3-nitrophenyl)-2-phenylpyrimidine dihydrochloride mp: 216° C. (dec.).

IR (Nujol): 1590, 1530, 1510, 1430, 1350 cm$^{-1}$.

Mass: 570 (M+).

(6) 5-(4-Isopropylcarbamoylmethylpiperazin-1-ylmethyl)-6-methyl-4-(3-nitrophenyl)-2-phenylpyrimidine mp: 172°–173° C.

IR (Nujol): 3490, 1665 cm$^{-1}$.

Mass: 488 (M+).

(7) 6-Methyl-5-(4-cyclopropylmethylpiperazin-1-ylmethyl)-4-(3-nitrophenyl)-2-phenylpyrimidine
mp: 180° C.
IR (Nujol): 1530, 1350, 1300 cm$^{-1}$.
Mass: 443 (M+).
(8) 6-Methyl-5-(4-methylpiperazin-1-ylmethyl)-4-(4-nitrophenyl)-2-phenylpyrimidine
mp: 138°–142° C.
IR (Nujol): 1605, 1540, 1525, 1495, 1410, 1350 cm$^{-1}$.
Mass: 403 (M+).
(9) 6-Methyl-5-(4-methylpiperazin-1-ylmethyl)-4-(2-nitrophenyl)-2-phenylpyrimidine
mp: 117°–119° C.
IR (Nujol): 1545, 1530, 1350, 1300 cm$^{-1}$.
Mass: 403 (M+).
(10) 6-Methyl-5-(4-methylpiperazin-1-ylmethyl)-4-(3-trifluoromethylphenyl)-2-phenylpyrimidine
mp: 159°–162° C.
IR (Nujol): 1545, 1330, 1320 cm$^{-1}$.
Mass: 426 (M+).
(11) 4-[2-(4-Chlorobenzyloxy)phenyl]-2,6-dimethyl-5-(4-methylpiperazin-1-ylmethyl)pyrimidine
mp: 110°–111° C.
IR (Nujol): 1600, 1550, 1300 cm$^{-1}$.
Mass: 436, 438 (M+).
(12) 5-(4-Methylpiperazin-1-ylmethyl)-4-(4-nitrophenyl)-2-phenylpyrimidine
mp: 194°–196° C.
IR (Nujol): 1565, 1535, 1520, 1425, 1350 cm$^{-1}$.
Mass: 389 (M+).

EXAMPLE 13

A mixture of 6-methyl-5-(4-formylpiperazin-1-ylmethyl)-4-(3-nitrophenyl)-2-phenylpyrimizine hydrochloride (3 g), methyl alcohol (30 ml), water (10 ml) and concentrated hydrochloric acid (6 ml) was stirred at 70° C. for 2 hours. The resulting precipitates were collected by filtration, washed with methyl alcohol and dried in vacuo to give 6-methyl-5-(1-piperazinylmethyl)-4-(3-nitrophenyl)-2-phenylpyrimidine dihydrochloride (2.86 g).
mp: 174° C. (dec.).
IR (Nujol): 1530, 1400, 1355 cm$^{-1}$.
NMR (DMSO-d$_6$, δ): 2.5–3.3 (8H, m), 2.82 (3H, s), 4.17 (2H, br s), 7.4–8.75 (9H, m)
Mass: 389 (M+).

EXAMPLE 14

A suspension of 6-methyl-4-(3-nitrophenyl)-5-phthalimidomethyl-2-phenylpyrimidine (6.9 g) and hydrazine monohydrate (0.8 g) in ethanol (140 ml) was refluxed for 6 hours. After filtering off the insolubles, the filtrate was poured into a suspension of chloroform (200 ml) and water (300 ml) under stirring. The organic layer was separated, washed with aqueous sodium chloride and dried over magnesium sulfate. The solvent was evaporated in vacuo and the resulting crystals were recrystallized from ethanol to give 5-aminomethyl-6-methyl-4-(3-nitrophenyl)-2-phenylpyrimidine (1.12 g).
mp: 145°–147° C.
IR (Nujol): 1545, 1520, 1360 cm$^{-1}$.
NMR (CDCl$_3$, δ): 2.80 (3H, s), 3.93 (2H, s), 7.4–7.6 (3H, m), 7.69 (1H, dd, J=8 Hz, 8 Hz), 8.15–8.6 (4H, m), 8.80 (1H, dd, J=2 Hz, 2 Hz).
Mass: 320 (M+).

EXAMPLE 15

A mixture of 5-acetyl-6-(2-dimethylaminoethyl)-4-(3-nitrophenyl)-2-phenylpyrimidine (1 g) and sodium borohydride (0.1 g) in methanol (40 ml) was stirred for 1 hour. The reaction mixture was poured into a mixture of water and chloroform and adjusted the pH to 9. The extract was dried over magnesium sulfate and evaporated in vacuo. The residue was chromatographed on silica gel eluting with a mixture of chloroform and methanol (20:1). The fractions containing the desired product were combined and concentrated in vacuo. The residue was recrystallized from diethyl ether to afford 6-(2-dimethylaminoethyl)-5-(1-hydroxyethyl)-4-(3-nitrophenyl)-2-phenylpyrimidine (0.2 g).
IR (Nujol): 3320, 1530, 1350 cm$^{-1}$.
NMR (CDCl$_3$, δ): 1.52 (3H, d, J=6 Hz), 2.86 (6H, s), 3.0–4.2 (4H, m), 5.1 (1H, q, J=6 Hz), 7.3–7.8 (4H, m), 7.85–8.55 (5H, m).
Mass: 392 (M+).

EXAMPLE 16

A mixture of 6-methyl-5-(4-formylpiperazin-1-ylmethyl)-4-(3-nitrophenyl)-2-phenylpyrimidine (4.5 g) and hydrochloric acid (2 ml) in methyl alcohol (45 ml) was stirred at 10° C. for 2 hours. The resulting precipitates were collected by filtration, washed with methyl alcohol and dried in vacuo to give 6-methyl-5-(4-formylpiperazin-1-ylmethyl)-4-(3-nitrophenyl)-2-phenylpyrimidine hydrochloride (4.14 g).
mp: 212°–214° C. (dec.).
IR (Nujol): 1675, 1545, 1525, 1350 cm$^{-1}$.
NMR (DMSO-d$_6$, δ): 2.5–4.0 (4H, m), 2.98 (3H, s), 4.42 (2H, s), 7.4–8.7 (10H, m).
Mass: 417 (M+).

What is claimed is:
1. Pyrimidine derivatives of the formula:

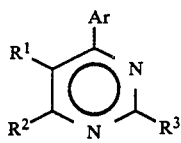

wherein
Ar is phenyl group substituted with 1 to 3 substituent(s) selected from the group consisting of nitro, halo(lower)alkyl, lower alkoxy and a group of the formula:

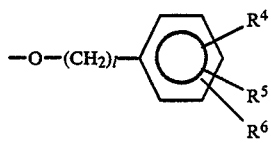

(in which l, R$^4$, R$^5$ and R$^6$ are each as defined in the below);
R$^1$ is lower alkoxycarbonyl group, lower alkanoyl group, hydroxy(lower)alkyl group or a group selected from the following formulas:

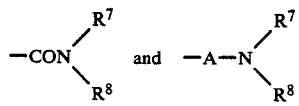

(in which $R^7$, $R^8$, and A are each as defined in the below);

$R^2$ is hydrogen, lower alkyl group or a group of the formula:

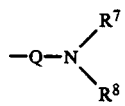

(in which Q, $R^7$ and $R^8$ are each as defined in the below);

$R^3$ is lower alkyl or phenyl group;

l is an integer of 0, 1 to 6;

$R^4$, $R^5$ and $R^6$ are each hydrogen or halogen;

$R^7$ and $R^8$ are each hydrogen, optionally substituted N-containing heterocyclic group selected from the group consisting of imidazolinyl and piperidyl or lower alkyl group optionally substituted with 1 to 3 substituent(s) selected from the group consisting of mono- or di(lower)alkylamino, and optionally substituted N-containing heterocyclic group selected from the group consisting of morpholinyl and pyrrolidinyl; or $R^7$ and $R^8$ are taken together to form an optionally substututed N-containing heterocyclic group with the adjacent nitrogen atom selected from the group consisting of 1-piperazinyl, 1-homopiperazinyl, morpholino, thiomorpholino, piperidino, 1,4-diazabicyclo [4.3.0]nonan-4-yl, 1-imidazolyl and phthalimido;

A and Q are each straight or branched lower alkylene group which may be substituted with a lower alkylidene;

provided that $R^1$ is a group of the formula:

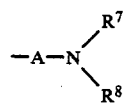

(in which $R^7$, $R^8$ and A are each as defined above) when $R^2$ is hydrogen or lower alkyl group; and their pharmaceutically acceptable salts.

2. A compound as claimed in claim 1, wherein $R^1$ is a group of the formula:

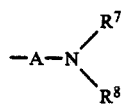

in which $R^7$, $R^8$ and A are each as defined in claim 1.

3. A compound as claimed in claim 2, wherein $R^7$ and $R^8$ are taken together to form an optionally substituted N-containing heterocyclic group with the adjacent nitrogen atom selected from the group consisting of 1-piperazinyl, 1-homopiperazinyl, morpholino, thiomorpholino, piperidino, 1,4-diazabicyclic [4.3.0]nonan-4-yl, 1-imidazolyl and phthalimido.

4. A compound as claimed in claim 3, wherein $R^7$ and $R^8$ are taken together to form 1-piperazinyl, 1-homopiperazinyl, morpholino or piperidino which may have 1 to 3 substituent(s) selected from the group consisting of hydroxy, lower alkyl, lower alkoxy, mono- or di-(lower)alkylamino-(lower)alkyl, hydroxy(lower)alkyl, cyclo(lower)alkyl(lower)alkyl, acyl, acyl(lower)alkyl, phenylsulfonyl optionally substituted with halogen, and a group of the formula:

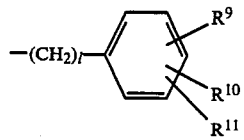

(in which l is as defined in claim 1, and $R^9$, $R^{10}$ and $R^{11}$ are each hydrogen or lower alkoxy).

5. A compound as claimed in claim 4, wherein $R^7$ and $R^8$ are taken together to form 1-piperazinyl which may be substituted with lower alkyl.

6. A compound as claimed in claim 5, wherein Ar is phenyl group substituted with a nitro group.

7. A compound as claimed in claim 6, wherein $R^2$ is hydrogen or lower alkyl group.

8. The compound as claimed in claim 7, which is 6-methyl-5-(4-methylpiperazin-1-ylmethyl)-4-(3-nitrophenyl)-2-phenylpyrimidine or its salt.

9. A compound as claimed in claim 1, wherein $R^1$ is lower alkoxycarbonyl group, lower alkanoyl group, hydroxy(lower)alkyl group or a group of the formula:

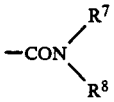

(in which $R^7$ and $R^8$ are each as defined in claim 1) and $R^2$ is a group of the formula:

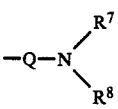

(in which $R^7$, $R^8$ and Q are each as defined in claim 1).

10. A pharmaceutical composition for the treatment of cerebrovascular disease, comprising an effective amount of a compound of claim 1 in association with a non-toxic, pharmaceutically acceptable carrier or excipient.

11. A method of treating cerebrovascular disease which comprises administering to a subject in need of said treatment an effective amount of a compound of claim 1.

* * * * *